United States Patent
Benadiková et al.

(10) Patent No.: US 11,059,797 B2
(45) Date of Patent: Jul. 13, 2021

(54) METHOD FOR PREPARATION OF 3,7-BIS-(DIMETHYLAMINO)-PHENOTHIAZIN-5-IUM CHLORIDE OR BROMIDE

(71) Applicant: MIKROCHEM spol, s r.o., Pezinok (SK)

(72) Inventors: Daniela Benadiková, Senkvice (SK); Juraj Cech, Pezinok (SK); Erik Juhás, Nová Dedinka (SK); Vladimír Oremus, Slovenský Grob (SK); Vendel Šmahovský, Pezinok (SK)

(73) Assignee: MIKROCHEM SPOL. S R.O., Pezinok (SK)

( * ) Notice: Subject to any disclaimer, the term of this patent is extended or adjusted under 35 U.S.C. 154(b) by 0 days.

(21) Appl. No.: 16/493,969

(22) PCT Filed: Mar. 15, 2018

(86) PCT No.: PCT/EP2018/056465
§ 371 (c)(1),
(2) Date: Sep. 13, 2019

(87) PCT Pub. No.: WO2018/167185
PCT Pub. Date: Sep. 20, 2018

(65) Prior Publication Data
US 2020/0010436 A1     Jan. 9, 2020

Related U.S. Application Data

(60) Provisional application No. 62/471,651, filed on Mar. 15, 2017.

(30) Foreign Application Priority Data

Mar. 15, 2017 (EP) .................................. 17161172

(51) Int. Cl.
C07D 279/20 (2006.01)
(52) U.S. Cl.
CPC .................. C07D 279/20 (2013.01)
(58) Field of Classification Search
CPC .................................................. C07D 279/20
USPC ........................................................ 544/36
See application file for complete search history.

(56) References Cited

U.S. PATENT DOCUMENTS

| 3,641,016 A | 2/1972 | Korosi |
| 2006/0079682 A1 | 4/2006 | Wassmann-Wilken et al. |

FOREIGN PATENT DOCUMENTS

| WO | 2008007074 A2 | 1/2008 |
| WO | 2015021500 A1 | 2/2015 |

OTHER PUBLICATIONS

International Preliminary Report on Patentability, issued in corresponding International Application No. PCT/EP2018/056465, dated Sep. 17, 2019, 9 pages.
International Search Report and Written Opinion issued in Application No. PCT/EP2018/056465, dated May 4, 2018, 12 pages.
N. Leventis, et al., "Synthesis of Substituted Phenothiazines Analogous to Methylene Blue by Electrophilic and Nucleophilic Aromatic Substitution in Tandem. A Mechanistic Perspective", Tetrahedron, vol. 53., No. 29, 1997, pp. 10083-10092.
A. Gollmer et al., "A Novel Set of Symmetric Methylene Blue Derivatives Exhibits Effective Bacteria Photokilling—a structure-response study", The Royal Society of chemistry and Owner Societies, Photochemical & Photobiological Sciences, vol. 14, No. 2, 2015, pp. 335-351.

*Primary Examiner* — Kahsay Habte
(74) *Attorney, Agent, or Firm* — Rothwell, Figg, Ernst & Manbeck, P.C.

(57) ABSTRACT

The present invention relates to: a process for preparing 3,7-bis-(dimethylamino)-phenothiazin-5-ium bromide or chloride; a method of converting 3,7-bis-(dimethylamino)-phenothiazin-5-ium bromide to 3,7-bis-(di-methylamino)-phenothiazin-5-ium chloride; and the purification of 7-bis-(di-methylamino)-phenothiazin-5-ium chloride by crystallization from aqueous solution of hydrochloric acid, leading to a pharmaceutically acceptable 3,7-bis-(di-methylamino)-phenothiazin-5-ium chloride (methylthioninium chloride, methylene blue, MTC) of formula I below reported.

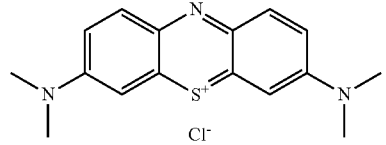

Formula I 3,7-bis(Dimethylamino)-phenothiazin-5-ium chloride

18 Claims, No Drawings

METHOD FOR PREPARATION OF 3,7-BIS-(DIMETHYLAMINO)-PHENOTHIAZIN-5-IUM CHLORIDE OR BROMIDE

CROSS REFERENCE TO RELATED APPLICATION

This application is a 35 U.S.C. § 371 National Stage of International Application No. PCT/EP2018/056465, filed 15 Mar. 2018, claims the benefit of U.S. Provisional Application No. 62/471,651, filed 15 Mar. 2017, and European Application No. 17161172.6, filed 15 Mar. 2017. Each application is incorporated herein by reference in its entirety.

BACKGROUND OF THE INVENTION

1. Field of the Invention

The present invention relates to: a process for preparing 3,7-bis-(dimethylamino)-phenothiazin-5-ium bromide or chloride; a method of converting 3,7-bis-(dimethylamino)-phenothiazin-5-ium bromide to 3,7-bis-(dimethylamino)-phenothiazin-5-ium chloride; and the purification of 7-bis-(dimethylamino)-phenothiazin-5-ium chloride by crystallization from aqueous solution of hydrochloric acid, leading to a pharmaceutically acceptable 3,7-bis-(dimethylamino)-phenothiazin-5-ium chloride (methythioninium chloride, methylene blue, MTC) of formula I below Formula I

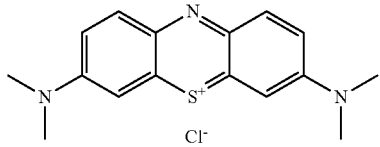

3,7-bis(Dimethylamino)-phenothiazin-5-ium chloride

2. Related Art 3,7-bis-(dimethylamino)-phenothiazin-5-ium chloride (also known as methythioninium chloride, Methylene Blue, MTC, C. I. Basic Blue, 9-methylthioninium chloride, Swiss Blue, C. I. 52015, C. I. Solvent Blue 8, Urolene Blue) is a well known phenothiazine dye for hair, leather and cellulosic fibers, a redox indicator, a photosensitizer for singlet oxygen generation, an antioxidant and an antiseptic stain for fixed and living tissue, diagnostic agent in renal function tests.

MTC is also used as a drug, for example as inhibitor of nitric oxide synthetase and guanylate cyclase. It has been found to improve the hypotension associated with various clinical states; it improves hypoxia and hyper dynamic circulation in cirrhosis of liver and severe hepatopulmonary syndrome. It also acts in transient and reproducible improvement of blood pressure and cardiac function in septic shock. In the past MTC has been used to treat malaria (P. Guttmann and P. Ehrlich, 1981); as a cure for methemoglobinemia and more recently was investigated for the photodynamic treatment of cancer. MTC is under evaluation in late-phase clinical development for the treatment of Alzheimer disease (Wischik et al. U.S. Pat. No. 7,737,138B2), and has recently been described as a diagnostic marker in the form of a visualizing dye in a variety of procedures, including sentinel lymph node biopsy in cancer patients (e.g., breast cancer patients), endoscopic evaluation of lesions in patients with GERD or Barrett's esophagus, urologic evaluation in patients with urethral or renal pelvis injury, and thoracoscopic procedures in patients with pulmonary nodules.

Methylene blue combined with light has been used to treat resistant plaque psoriasis, AIDS-related Kaposi's sarcoma, West Nie virus, and to inactivate *Staphylococcus aureus*, HIV-1, Duck hepatitis B virus, adenovirus vectors, and hepatitis C. Phenothiazine dyes and light have been known to have virucidal properties for over 70 years. However, in some circumstances, the combination of phenothiazine dyes and light can cause DNA damage that may lead to cancer.

MTC has been used in the form of tablet or in an injection form. The wide use of MTC as a pharmaceutical requires synthetic methods able to afford the synthesis of product with high chemical purity.

The synthesis, purification and biological activity of MTC are described in numerous patents and publications.

3,7-Bis(dimethylamino)-phenothiazin-5-ium chloride (MTC) was originally synthesized by the German chemist H. Caro in 1876, and has been commercially available since its first production by BASF in 1876 (German patent No. DE-1886, Badishe Anilin-und Soda Fabrik, 1877). According to the BASF's patent, MTC was synthesized by nitrosylation of dimethylaniline, subsequent reduction to form N,N-dimethyl-1,4-diaminobenzene, and subsequent oxidative coupling using hydrogen sulfide and iron (III) chloride. Later many authors described similar methods for the synthesis of MTC. In principle the methods are the same, and only the reagents used are different. A. Bernthsen (1885a, 1885b and 1889), H. E. Fierz-David and L. Blangley (1949) published the preparation of MTC from dimethylaniline as is illustrated in the Scheme 1. An analogous method is described in Colour Index (Vol. 4 $3^{rd}$ Edition, 1971)

According to Scheme 1 the starting material dimethylaniline in step i is nitrosilated by reaction with sodium nitrite in aqueous hydrochloric acid. In step ii the nitroso compound is reduced to dimethylamino aniline using zinc dust and additional hydrochloric acid. Dimethylamino aniline is oxidised (step iii) with thiosulfonic acid in sulphuric acid in presence of zinc chloride to give the thiosulfonic acid derivative of p-aminodimethyl amine, in step iv the thiosulfonic acid p-aminodimethyl amine is oxidised to thiosulfonic acid of Bindschedler green (chemical name N-[4-[[4-(dimethylamino)-2-(sulfothio)phenyl]imino]-2,5-cycohexadien-1-ylidene]-N-methyl-Methanaminium). The ring closure to produce MTC (step v) is carried out in the presence of manganese dioxide or copper sulphate.

Scheme 1

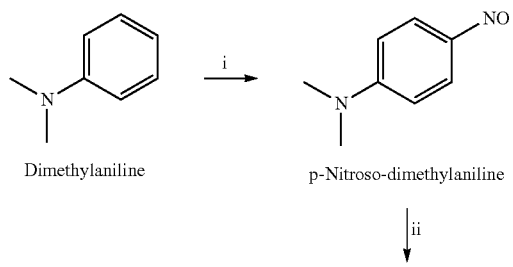

Dimethylaniline → p-Nitroso-dimethylaniline ii

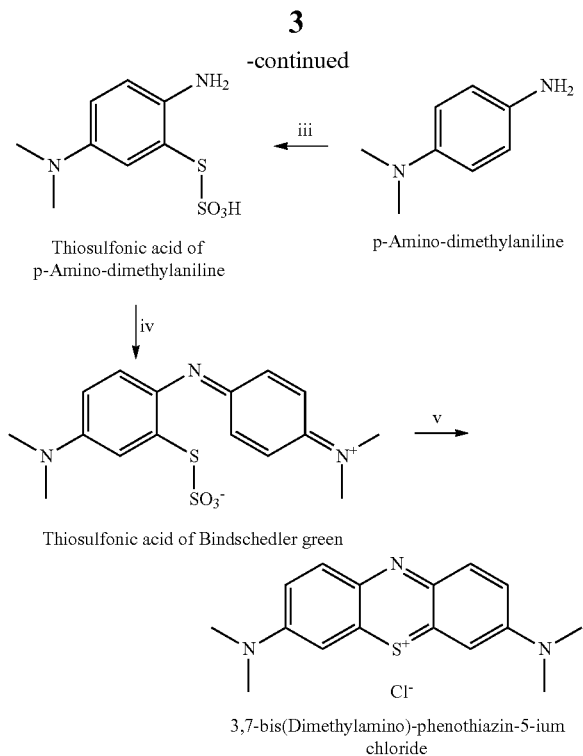

Wista Laboratories (WO2010/130977) tried to eliminate heavy metals from the synthetic pathway by using alkaline metal persulfate and ammonium persulfate with sodium bichromate as an oxidation agent. Using the same steps as Scheme 1 with some improvements, they described preparation in a 3-pot method (three reactors), where a major part of the synthetic preparation was carried out in POT 1 (first reactor), followed by POT 2 cyclisation (second reactor) and POT 3 which was recrystalisation of MTC (third reactor).

Additionally, they described a 2-pot method, where recrystalization was carried out in the second reactor.

Purification of MTC is described for example by P. N. Marshall and S. M. Lewis Stain Technol. 1975a, 1975b; 50(6), 375-81 and 143-147 through solvent extraction followed by crystallization, W. Löhr et al. (The azure dyes: their purification and physicochemical properties. I. Purification of Azure B, Stain Technologies (1974) 49(6), 359-366 and by H. E. Fierz-David (Fundamental Processes of Dye Chemistry (1949), Interscience deel, Oxazine and Thiazine Dyes) through the formation of zinc chloride double salt. MTC prepared according to the above cited method, depicted in Scheme 1, contain large amount of metal impurities, such as Cu, Fe, Cr, Mn, Al, Zn, exceeding the safety limits set by European Health Agencies.

A different approach was published by C. M. Wischik at al., where commercially available MTC was used in technical grade with purity less than 95% (WO2008/007074). This was first reduced by sodium borohydride (or, alternatively, by hydrazine, methylhydrazine) to white (colorless) reduced form (leucoform), and subsequently was acylated with acetic anhydride. The crystallisation of the acetyl derivative afforded a purified product without metals. The acetyl derivative was hydrolyzed back to the white reduced form of MTC and in a final step was oxidized to MTC (blue colored), which, compared to the technical grade MTC used as starting material, had a much higher purity. For the oxidation reaction iron (III) chloride, isoamyl nitrite, t-butylamyl nitrite and amberlite were used (see Scheme 2). In the same international patent application is also described the preparation of 1-acetyl-3,7-dimethylaminophenotiazine intermediate through a sequence of reactions which include the nitration of phenothiazine with sodium nitrite, the N acetylation using acetic anhydride to afford 3,7-dinitro-10-acetyl phenothiazine which was reduced in hydrogen atmosphere using palladium on active carbon as catalyst and finally reacted with p-formaldehyde and sodium cyanoborohydride

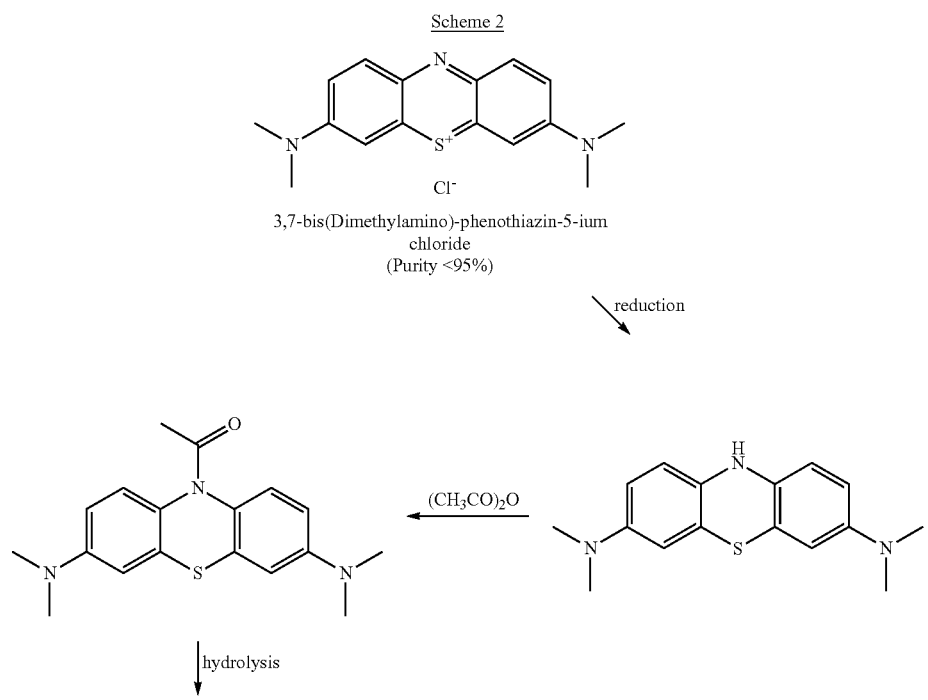

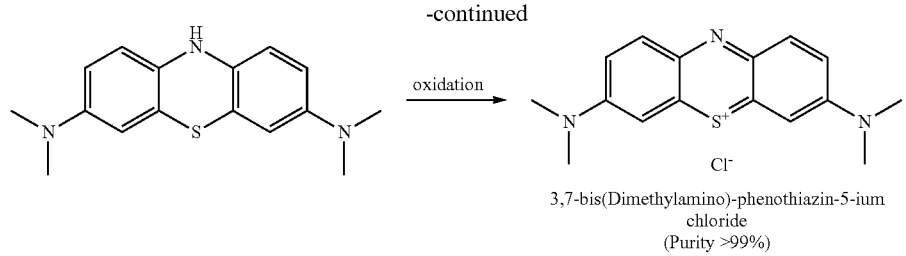

3,7-bis(Dimethylamino)-phenothiazin-5-ium
chloride
(Purity >99%)

M. Feraud et al. found a new synthetic pathway and developed its chemical process leading to the manufacturing of pharmaceutical grade methylene blue (WO2008/006979). In this patent the purification of crude MTC through a sequence of steps including benzoylation of crude MCT is described, which leads to formation of the corresponding, benzoyl reduced form, followed by crystallization, oxidation with 2,3-dichloro-5,6-dicyano-1,4-benzoquinone (DDQ) and a final purification performed sequentially by ion exchange chromatography and crystallization of product from aqueous medium (see Scheme 3).

Scheme 3

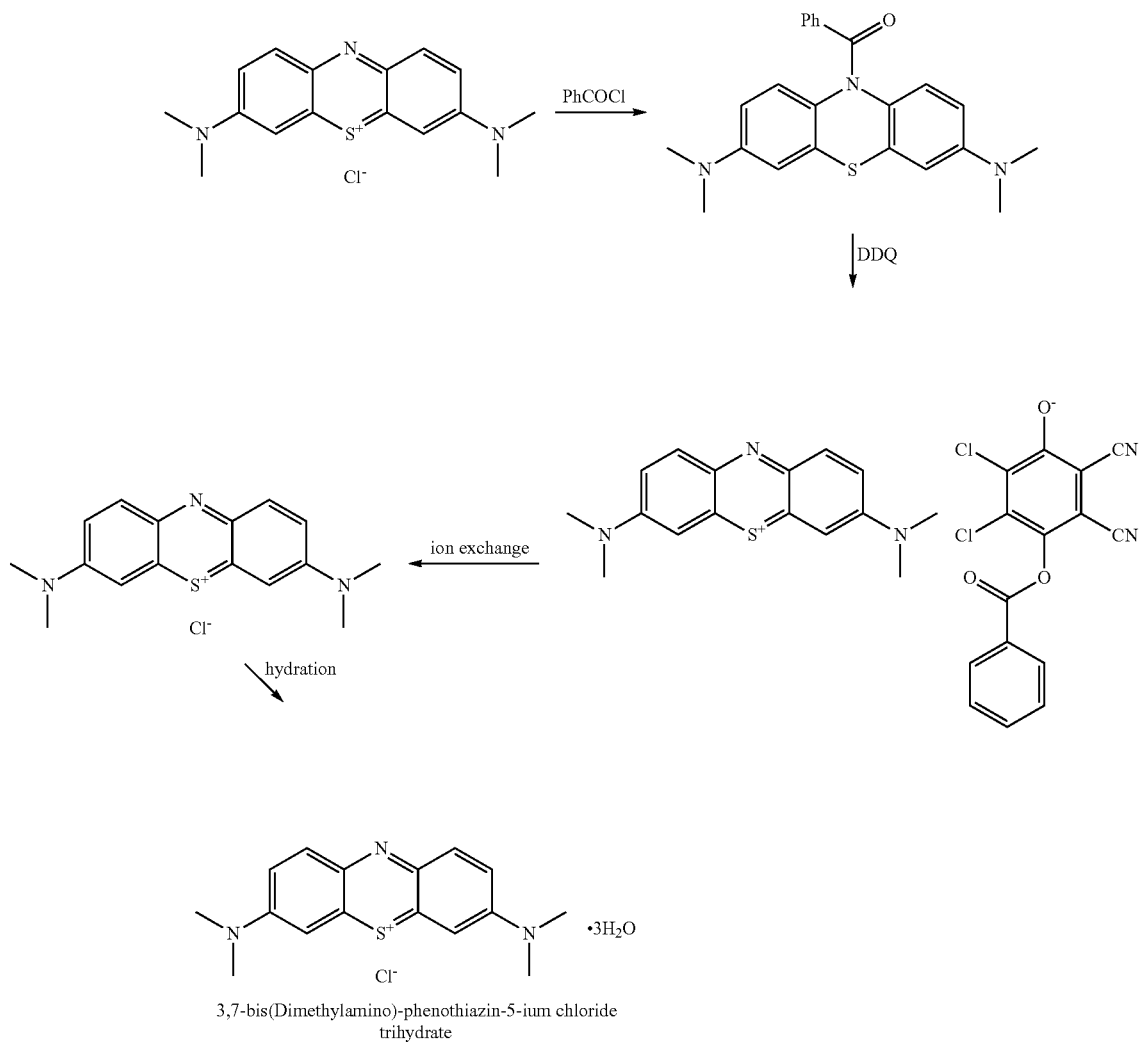

3,7-bis(Dimethylamino)-phenothiazin-5-ium chloride
trihydrate

E. Malvin in WO2015/021500 describes purification of technical grade MTC using ascorbic acid to produce leucomethylene blue and subsequent oxidation with p-benzoquinone (see Scheme 4).

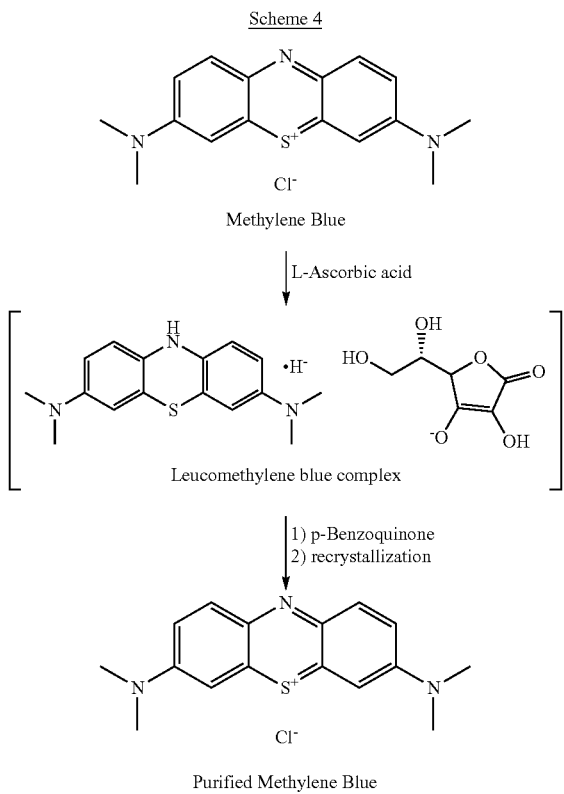

Scheme 4

MTC can also be prepared from phenothiazine, using a nitration reaction. A slight modification of this process uses in a first step bromine for bromination of phenothiazine at positions 3 and 7 together with simultaneous preparation of 3,7-dibromophenothiazine-5-ium bromides followed by reaction with dimethylamine to obtain the bromide form of MTC (see Scheme 5). In literature this preparation method of MTC is known as Kehrmann's Synthese (Kehrmann F. Ber., 1916, 49, 53; Kehrmann F.: Diserens L. Ber., 1915, 48, 318) and is currently used for manufacturing of MTC.

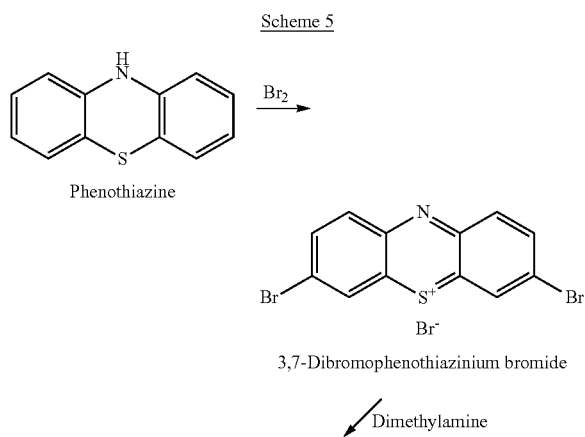

Scheme 5

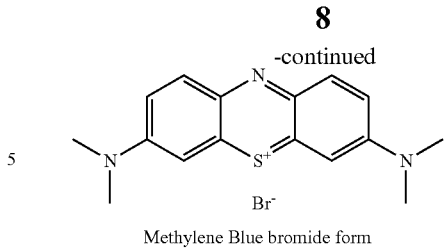

Methylene Blue bromide form

A slight modification of the Kehrmann's synthetic method was used by N. Leventis et al. Tetrahedron Vol. 53 No 29, pp 10083-10092 (1997) for the preparation of MTC analogues starting from phenothiazine. Leventis et al. described a 2-step process, starting with the conversion of phenothiazine into 3,7-dibromophenothiazin-5-ium bromide through a reaction with bromine in acetic acid, followed by an aromatic nucleophilic substitution reacting the 3,7-dibromophenothiazin-5-ium bromide with a di-substituted amine in ethanol or chloroform as a solvent, with formation of the bromide salt of the MTC analogs. The above process had low yields (27-63%) when the divinyl analogue of methylene blue was prepared, but had good yield (70-85%) in the preparation of methylene blue (bromide salt). However, this process had some disadvantages: it required large amounts of bromine in step 1 (a 20-molar excess of bromine) to achieve a complete conversion of phenothiazine into 3,7-dibromophenothiazin-5-ium bromide, since the use of lower amounts afforded a mixture of 3,7-dibromophenothiazin-5-ium bromide (oxidized form) and 3,7-dibromophenothiazine (reduced form, by-product); the 3,7-dibromophenothiazin-5-ium bromide had to be isolated and purified, since this substance is not very stable, especially in solution; moreover, in the second step, the selected solvent (ethanol) competed with the di-substituted amine for the nucleophilic substitution, with formation of by-products.

Common disadvantages of the cited synthetic methods are low yields of the product, due to the low regioselectivity of the reaction, the need to isolate 3,7-dibromophenotiazin-5-inum bromide before the next reaction step; long reaction times; the use of huge amount of solvents for reaction and separation of intermediates; and the necessity to use large molar excess of bromine.

Moreover, the wide use of MTC as pharmaceutical requires a very pure substance containing only traces of metals.

SUMMARY OF THE INVENTION

One objective of the present invention is to provide an improved process for producing 3,7-bis-(dimethylamino)-phenothiazin-5-ium bromide or chloride within the quality standards set by the US and European Health Agencies, suitable for use as a pharmaceutical. In one embodiment, the present invention is a process to produce 3,7-bis-(dimethylamino)-phenothiazin-5-ium bromide or chloride, having quality attributes meeting US and EU Health Agencies, which can be carried out in a fast and economically advantageous way. In particular, the process of this invention allows for performing 2 chemical steps of the process, namely the conversion of phenothiazine into the corresponding 3,7-dialogenophenothiazin-5-ium halide and the subsequent transformation of this 3,7-dialogenophenothiazin-5-ium halide into 3,7-bis-(dimethylamino)-phenothiazin-5-ium bromide or chloride, as a one-pot reaction, which is carried out in the same reaction vessel and using one solvent system common for both reaction steps.

Advantageously, the particular process of the invention does not use the isolation and/or purification of any reaction intermediate after reacting phenothiazine with a suitable halogen, before proceeding with the subsequent process steps. The process of the invention allows for the elimination of the time needed for isolation and purification of intermediates, for the decrease of the production wastes, the elimination of the risk that instable intermediates could degrade during isolation/purification steps, and the use of non-toxic solvents. Therefore, the process of the invention constitutes a great improvement over the prior art.

DETAILED DESCRIPTION OF THE INVENTION

One objective of the present invention is to provide an improved method for producing 3,7-bis-(dimethylamino)-phenothiazin-5-ium bromide or chloride within the standards set by the US and European Health Agencies, suitable for pharmaceutical use.

The present invention provides a process for producing 3,7-bis-(dimethylamino)-phenothiazin-5-ium bromide or chloride (Scheme 6 and Scheme 7) comprising the steps of:
 (a) reacting chlorine or bromine with phenothiazine, optionally in the presence of a suitable metal catalyst, to produce 3,7-dichloro-phenothiazin-5-ium chloride or 3,7-dibromo-phenothiazin-5-ium bromide respectively;
 (b) adding dimethylamine to the reaction mixture of step (a) to produce 3,7-bis-(dimethylamino)-phenothiazin-5-ium chloride or 3,7-bis-(dimethylamino)-phenothiazin-5-ium bromide respectively;
 (c) optionally, purification of 3,7-bis-(dimethylamino)-phenothiazin-5-ium chloride or 3,7-bis-(dimethylamino)-phenothiazin-5-ium bromide obtained in step (b), preferably by slurring these compounds in a suitable solvent or solvent mixture;
 (d) optionally, eluting the bromide material of step (b) or (c) into an ion exchange column, to exchange bromide with chloride;
 (e) optionally, dissolving 3,7-bis-(dimethylamino)-phenothiazin-5-ium chloride (MTC) or 3,7-bis-(dimethylamino)-phenothiazin-5-ium bromide of step (b) or (c) in aqueous solution of hydrochloric acid and purifying the products; and
 (f) optionally, crystallizing 3,7-bis-(dimethylamino)-phenothiazin-5-ium chloride (MTC) or 3,7-dibromo-phenothiazin-5-ium bromide of step b), c) or d).
wherein the said first (a) and second (b) steps are carried out without isolation and/or purification of the intermediates formed in step (a) (3,7-dichloro-phenothiazin-5-ium chloride or 3,7-dibromo-phenothiazin-5-ium bromide).

According to the present invention, the steps (a) and (b) of the process are a one pot reaction, which is carried out in the same reaction vessel and using one solvent system common for both reaction steps. Step (d), which is the conversion from the bromide form to the chloride form, is optional and is carried out when the material obtained in step (c) is 3,7-bis-(dimethylamino)-phenothiazin-5-ium bromide.

To obtain the 3,7-bis-(dimethylamino)-phenothiazin-5-ium chloride (MTC), the step (d) of eluting the material of step (c) into an ion exchange column to exchange bromide with chloride is necessary when the material obtained in step (c) is 3,7-bis-(dimethylamino)-phenothiazin-5-ium bromide.

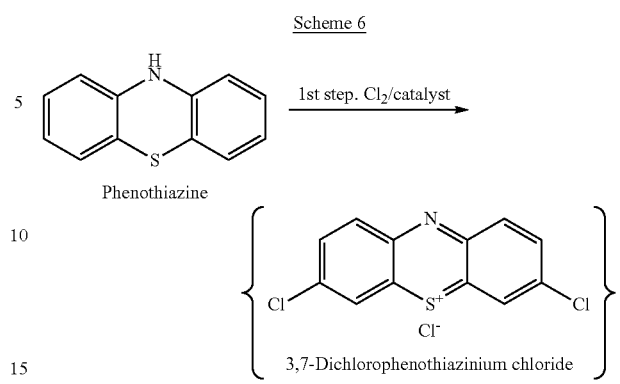

Scheme 6

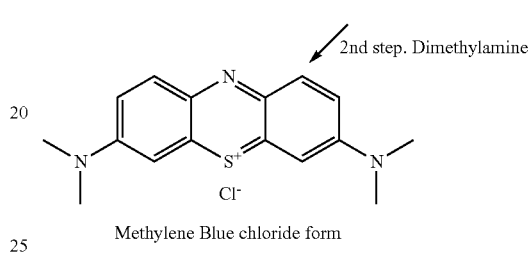

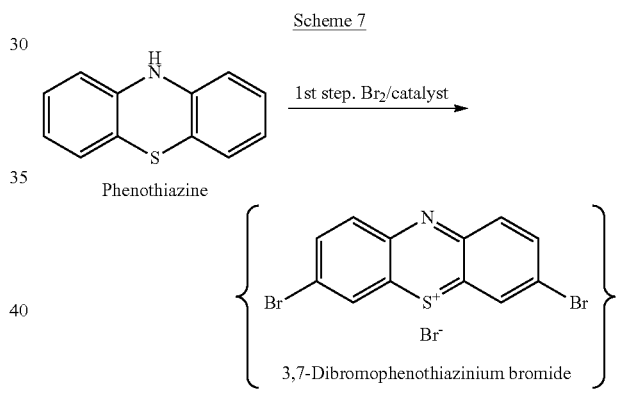

Scheme 7

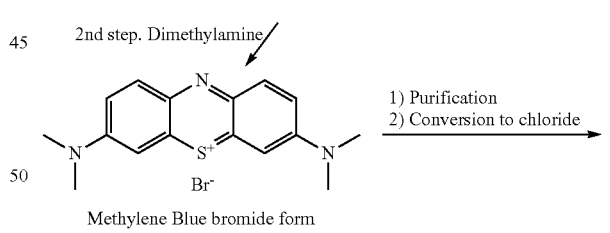

Advantageously, the process of this invention produces MTC in two reaction steps, (a) and (b), which are carried out in the same reaction vessel without for the necessity of separation and purification of the intermediates between these steps, allows for the elimination of the time needed for isolation and purification of intermediates and allows for an increase in the space-time yields of reactors. In addition, since both reaction steps (a) and (b) utilize the same solvent system, the process of the invention does not require a process of solvent change after the step (a) to change it with a different solvent to carry out step (b). Moreover, the process of the invention allows a reduction of the molar excess of chlorine or bromine in reaction step (a) with respect to phenothiazine compared to what is reported in the prior art. The reduction of the molar equivalents of bromide or chlorine in step (a) and the unique solvent system for steps (a) and (b) allows a significant reduction of the solvent wastes, which represents, working on industrial scale, a huge cost reduction. A further advantage of the process of the invention is that the elimination of the need to isolate and purify the 3,7-dibromophenothiazin-5-ium bromide or 3,7-dichlorophenothiazin-5-ium chloride after step (a) allows for reducing the risk that those substances, which are known to be quite unstable, especially in solution, could degrade during the isolation and/or purification step. A further advantage of the process of the invention is that it allows the use of solvents with low toxicity, for example, ethylacetate. This last aspect of the present invention is particularly favorable when the product of the chemical process is an active pharmaceutical ingredient for which the use of solvents with low toxicity is strongly recommended by the guidelines of the main health agencies like EMEA and FDA (ref. ICH guideline Q3(R5)). The process uses cheap purification procedures of the final product affording MTC with a very low content of by-products and metals, therefore the product is suitable for pharmaceutical use.

In one embodiment, the present invention is the "not isolated" intermediate obtained from the step (a) of the Scheme 6, namely 3,7-dichlorophenotiazin-5-ium chloride. This compound has been isolated and characterized by the present inventors for analytical purpose only.

One embodiment of the present invention is 3,7-dichlorophenotiazin-5-ium chloride.

One embodiment of the present invention is 3,7-dichlorophenotiazin-5-ium chloride for use as an intermediate.

In one embodiment, the invention is a process for producing 3,7-bis-(dimethylamino)-phenothiazin-5-ium chloride (MTC) or bromide comprising the steps of:
 a) reacting chlorine or bromine with phenothiazine, to produce 3,7-dichloro-phenothiazin-5-ium chloride or 3,7-dibromo-phenothiazin-5-ium bromide respectively;
 b) adding dimethylamine to the reaction mixture of step a), to produce 3,7-bis-(dimethylamino)-phenothiazin-5-ium chloride or 3,7-bis-(dimethylamino)-phenothiazin-5-ium bromide respectively;
wherein steps a) and b) are carried out without isolation and/or purification of the intermediate formed in the step a). In one embodiment, in step (a) of the process of the invention, phenothiazine is dissolved in a solvent system which is contacted with chlorine or bromine to yield a 3,7-dichlorophenothiazine chloride or 3,7-dibromophenothiazine bromide intermediate. All molar ratios of chlorine or bromine:phenothiazine higher than 1:1 are suitable for the step (a) of the process of this invention, provided that 3,7-dichlorophenothiazine chloride or 3,7-dibromophenothiazine bromide are obtained as intermediates. Suitable molar ratios of chlorine or bromine to phenothiazine in step (a) are typically in the range from about 1:1 to about 4:1 bromine or chlorine:phenothiazine, preferably from about 2.2:1 to about 2.8:1 bromine or chlorine:phenothiazine. In some embodiments, the molar ratio of chlorine or bromine to phenothiazine in step (a) is about 2:1 bromine or chlorine:phenothiazine. In some embodiments, the molar ratio of chlorine or bromine to phenothiazine in step (a) is about 2.5:1 bromine or chlorine:phenothiazine. In some embodiments, the molar ratio of chlorine or bromine to phenothiazine in step (a) is about 3:1 bromine or chlorine:phenothiazine. In a preferred embodiment, the molar ratio of chlorine or bromine to phenothiazine in step (a) is about 2.5:1 bromine or chlorine:phenothiazine. In a further preferred embodiment, the molar ratio of chlorine or bromine to phenothiazine in step (a) is about 3:1 bromine or chlorine:phenothiazine.

The step (a) of the process of the invention can, in some embodiments, be carried out in the presence of an inert solvent.

The term "inert" means that the solvent is non-reactive towards the reagents and products and does not interfere with the process of this invention. Any inert solvent is suitable so long as it provides the intended solubilization, and so long as the 3,7-dichlorophenothiazine chloride or 3,7-dibromophenothiazine bromide are obtained as intermediates.

Suitable inert solvents for step (a) include polar protic and aprotic organic solvents, such as dichloromethane, acetic acid, methylacetate, ethylacetate, butylacetate, chloroform or mixtures thereof. In one embodiment, the solvent is dichloromethane. In one embodiment, the solvent is methyl acetate. In one embodiment, the solvent is butyl acetate. In a preferred embodiment, the solvent is ethyl acetate. In some embodiments, bromine or chlorine are added to the reaction mixture of step (a) in form of solutions in said inert solvent. In other embodiments, bromine or chlorine are added into the reaction mixture of step (a) directly as pure substances, i.e. in liquid or in gaseous form, respectively. As a general rule, the volume/mass ratio between solvent and phenothiazine is between about 1 and about 40, and is preferably between about 2.5 and about 25. In one embodiment, the reaction of phenothiazine with bromine or chlorine in step (a) is carried out in the absence of catalyst. In one embodiment, the reaction of phenothiazine with bromine or chlorine in step (a) takes place in the presence of a metal catalyst. The metal catalyst can be used in its anhydrous form or in all its states of hydration. The metal catalyst which is employed in step (a) of the reaction can be any which produces desired intermediates. In some embodiments, said metal catalyst is selected from the Group VIII metals of the Periodic Table, for example, iron, cobalt, nickel. In other embodiments, said metal catalyst is selected in the group IB metals of the Periodic Table, for example, copper and/or silver. In other embodiments, said metal catalyst is selected in the group IIIB metals of the Periodic Table, such as, by way of example, aluminum. In some embodiments, the metal catalyst is added to the reaction mixture in step (a) in elemental form. In other embodiments, the metal catalyst is added to the reaction mixture in step (a) in form of salt. According to the latter embodiments, suitable salts of the above metals may be selected from the group comprising, but not limited to: chlorides, bromides, iodides, fluorides, carbonates, nitrates, sulfates, phosphates, citrates, acetates, maleates. In other embodiments, the metal catalyst is in the form of an oxide. In one embodiment, the metal catalyst of step (a) is iron. In a preferred embodiment, the metal catalyst of step (a) is an iron salt. According to the latter embodiment, said iron salt can be an iron (II) salt or an iron (III) salt, preferably an iron (III) salt. The iron (III) salt can be used in its anhydrous form or in all its states of hydration forms. In a more preferred embodiment, the Iron(III)chloride is used in its hexahydrate form. In some embodiments, said iron (II) salt can be selected from the group comprising, but not limited to: iron (II) chloride, iron (II) bromide, iron (II) iodide, iron (II) fluoride, iron (II) carbonate, iron (II) nitrate, iron (II) sulfate, iron (II) phosphate, iron (II) acetate, iron (II) maleate. In some embodiments, said iron (III) salt can be selected from the group comprising, but not limited to: iron (III) chloride, iron (III) bromide, iron (III) iodide, iron (III) fluoride, iron (III) carbonate, iron (III) nitrate, iron (III) sulfate, iron (III) phosphate, iron (III) acetate, iron (III) maleate. In a preferred embodiment, said iron (II) salt is iron (II) sulfate. In a preferred embodiment, said iron (III) salt is iron (III) chloride.

Despite the knowledge in the field, it has in fact surprisingly been discovered by the present inventors that the metal catalysis above described can be usefully obtained also using an iron (II) salt, preferably iron (II) sulfate.

Any hydrate form of the iron salts above can be used according to the invention.

Any operable process conditions can be employed in the process of this invention provided that the desired intermediate products are formed. According to the process of the invention, the process temperature ranges for step (a) are from about −35° C. to about 45° C., preferably from about −30° C. to about 35° C., more preferably from about −20° C. to about 15° C., much more preferably from about −20° C. to about −10° C. In one preferred embodiment, the temperature for step (a) is of about −15° C. In one embodiment, the temperature of step (a) is maintained in the range between about −25° C. to about 0° C. In another embodiment, the temperature of step (a) is maintained in the range between about −20° C. to about −5° C. In a preferred embodiment, the temperature of step (a) is maintained in the range between about −20° C. to about −10° C. In one preferred embodiment, the temperature of step (a) is maintained at about −15° C. In one embodiment, step (a) is conducted at a temperature of less than about 45° C., 35° C., 25° C., 15° C., 10° C., 5° C., 0° C., −5° C., −10° C., −15° C., −20° C. or −25° C. In one embodiment, step (a) is conducted at a temperature of less than about 25° C. In one embodiment, step (a) is conducted at a temperature of less than about 0° C. In one embodiment, step (a) is conducted at a temperature of less than about −10° C. In one preferred embodiment, step (a) is conducted at a temperature of between about −20° C. and about −10° C. In one more preferred embodiment, step (a) is conducted at a temperature of about −15° C.

The reaction times of step (a) depend on the reaction temperature, the rate of mixing of reactants and the concentration of reactants in the reaction zone. In one embodiment, optionally in a batch reactor, the reaction time of step (a) is equal to or less than about 6 hours. In one embodiment, the reaction time of step (a) is about 5 hours. In one embodiment, the reaction time of step (a) is about 4 hours. In one embodiment, the reaction time of step (a) is about 3 hours. In one embodiment, the reaction time of step (a) is about 2 hours. In some embodiments, the reaction time of step (a) is about 3 hours, preferably about 2 hours, more preferably about 1 hour. In a preferred embodiment, the reaction time of step (a) is about 1 hour. The reaction times may be properly adapted based on the reaction vessels and the process scale (for example, passing from pilot to industrial scale)

In one embodiment of the present invention, the step (b) of the process of the present method can be carried out by addition of dimethylamine into the reaction mixture rich in 3,7-dichlorophenothiazine chloride or 3,7-dibromophenothiazine bromide formed in step (a), without any intermediate purification or isolation step. In one embodiment, said dimethylamine is added to the reaction mixture of step (b) as pure dimethylamine. According to such embodiment, said pure dimethylamine can be in gaseous or liquid form. According to another embodiment, said dimethylamine is added to the reaction mixture of step (b) in form of a solution in a suitable solvent. According to such embodiment, said suitable solvent should be inert and can be selected from the group comprising, but not limited to: methanol, water, butyl acetate and ethyl acetate, and mixtures thereof. According to a preferred embodiment, said dimethylamine is added to the reaction mixture of step (b) in form of solution in ethyl acetate. According to a preferred embodiment, said dimethylamine is added to the reaction mixture of step (b) in form of solution in methanol. Suitable molar ratio of chlorine or bromine used in step (a) to dimethylamine used in step (b) is in the range of about 1:1 to about 1:5, preferably in the range of about 1:1.5 to about 1:4.5, more preferably in the range of about 1:2.0 to about 1:4.0 bromine or chlorine: dimethylamine. In one embodiment, the molar ratio of chlorine or bromine used in step (a) to dimethylamine used in step (b) is about 1:2. In another embodiment, the molar ratio of chlorine or bromine used in step (a) to dimethylamine used in step (b) is about 1:2.6. In another embodiment, the molar ratio of chlorine or bromine used in step (a) to dimethylamine used in step (b) is about 1:3.0. In another embodiment, the molar ratio of chlorine or bromine used in step (a) to dimethylamine used in step (b) is about 1:3.4. In another embodiment, the molar ratio of chlorine or bromine used in step (a) to dimethylamine used in step (b) is about 1:4.0. In a preferred embodiment, the molar ratio of chlorine or bromine used in step (a) to dimethylamine used in step (b) is about 1:3.0. In a preferred embodiment, the molar ratio of chlorine or bromine used in step (a) to dimethylamine used in step (b) is about 1:3.1.

According to the process of the invention, the reaction of step (b) can be carried out at a temperature of from about −35° C. to about 45° C., preferably at a temperature from about −30° C. to about 35° C., more preferably at a temperature from about −25° C. to about 20° C., much more preferably at a temperature from about −20° C. to about 10° C. In one preferred embodiment, step (b) is carried out at a temperature of about −15° C.

In one embodiment, the temperature of step (b) is maintained in the range between about −25° C. to about 25° C. In another embodiment, the temperature of step (b) is maintained in the range between about −20° C. to about 20° C. In another embodiment, the temperature of step (b) is maintained in the range between about −20° C. to about 15° C. In a preferred embodiment, the temperature of step (b) is maintained in the range between about −20° C. to about 10° C. In one preferred embodiment the temperature of step (b) is maintained at about −15° C.

In one embodiment step (b) is conducted at a temperature of less than about 45° C., 40° C., 35° C., 30° C., 25° C., 20° C., 15° C. or 10° C. In one embodiment step (b) is conducted at a temperature of less than about 25° C. In one embodiment step (b) is conducted at a temperature of less than about 20° C. In one embodiment step (b) is conducted at a temperature of less than about 10° C. In one preferred embodiment, step (b) is conducted at a temperature of between about −15° C. and about 10° C.

In one embodiment, step (a) is conducted at a temperature of less than about 0° C., preferably less than about −10° C., more preferably between about −20° C. and about −10° C. and step (b) is conducted at a temperature of less than about 20° C., preferably less than about 10° C., more preferably between about −20° C. and about 10° C. In one preferred embodiment, step (a) is conducted at a temperature of about −15° C. and step (b) is conducted at a temperature of about −15° C.

Reaction times of step (b) depends on the reaction temperature, the rate of mixing of reactants and the concentration of reactants in the reaction zone. In one embodiment, optionally in a batch reactor, the reaction time of step (b) is equal to or less than about 6 hours. In one embodiment, the reaction time of step (b) is about 5 hours. In one embodiment, the reaction time of step (b) is about 4 hours. In one embodiment, the reaction time of step (b) is about 3 hours. In one embodiment, the reaction time of step (b) is about 2 hours. In some embodiments, the reaction time of step (b) is about 3 hours, preferably about 2 hours, more preferably about 1 hour. In a preferred embodiment, the reaction time of step (b) is about 2 hours.

The reaction times may be property adapted based on the reaction vessels and the process scale (for example, passing from pilot to industrial scale).

In one embodiment of the present invention, steps (a) and (b) are carried out in the same reaction vessel and in the same solvent system. Since the regioselectivity of reaction in the step (a) of the process is high, the separation and purification of the main intermediates formed in the step (a) is not needed. Not wishing to be bound by theory it is believed that the high regioselectivity of the step (a) is due to at least in part by the selected temperature ranges or by the combination of the temperature ranges and the selected solvent. The reaction mixture from the step (a) is directly used for reaction with dimethylamine.

In the process of the invention, the final reaction products of step (b), 3,7-bis-(dimethylamine)-phenothiazin-5-ium chloride or bromide, are solids which are only slightly soluble in the inert solvent used for both reactions of steps (a) and (b). Said reaction products can be separated from the reaction mixture by using common solid-liquid separation techniques well known in the art, such as, by way of example, filtration, or sedimentation, or centrifugation.

In one embodiment, after separation of the raw product obtained after step (a) and (b) from the reaction mixture by using a common solid-liquid separation technique, the solid raw product is washed with the used inert solvent system and subsequently with a diluted aqueous solution of hydrochloric acid. The concentration of hydrochloric acid is in the range from about 0.05M to about 2.0M, preferably from about 0.1M to about 1.0M, more preferably from about 0.1M to about 0.4M. After washing, dimethylamine hydrobromide or hydrochloride, generated in process, are removed from the desired products.

According to the invention, further purification of the products obtained from step (a) and (b) can be carried out to obtain a very low concentration of by-products and metals (within the specifications of the US and European pharmacopoeia monographs). Such purification (step (c)) may comprise different steps of slurring 3,7-bis-(dimethylamine)-phenothiazin-5-ium chloride or bromide under stirring at different temperatures and with suitable solvent. In one embodiment, said purification comprises the following steps:

1) slurring said products from steps (a) and (b) with a solvent or solvent mixtures at a temperature within the range from about 2° C. to about 35° C., preferably from about 5° C. to about 30° C., more preferably from about 20° C. to about 25° C.;
   slurring said products from steps (a) and (b) with a solvent or solvent mixtures, at a temperature within the range from about 25° C. to about 75° C., preferably from about 30° C. to about 65° C., more preferably from about 40° C. to about 60° C.; and, optionally,
2) slurring again said products from steps (a) and (b) with a solvent or solvent mixtures at a temperature within the range from about −5° C. to about 20° C., preferably from about 0° C. to about 15° C., more preferably from about 5° C. to about 10° C.

Any of the above steps may be repeated several times in order to obtain a product of the desired quality, having very low concentration of by-products and metals (within US and European pharmacopoeia monographs). After each step, the solid material can be separated from the washing solvent through a common solid-liquid separation technique well known in the art, such as, by way of example, filtration, or sedimentation, or centrifugation. Advantageously, before any step of separation of solids from the liquid phase, the mixture to be filtered off must be at a temperature equal to or lower than about 30° C., in order to maximize the yield of the solid. The separation step is carried out at a temperature equal to or below about 30° C., preferably within the range from about −5° C. to about 25° C., more preferably from about 0° C. to about 15° C., much more preferably from about 5° C. to about 10° C.

Suitable solvents or solvent mixtures for purification include polar aprotic and/or protic solvents. Said polar protic and aprotic solvents comprise, but are not limited to: dichloromethane, methylacetate, ethylacetate, butylacetate, methanol, ethanol, 2-propanol, hydrochloric acid, water or mixtures thereof. Preferably, pure alcohols or aqueous alcohols mixtures with a relative v/v ratio ranging from 1/4 to 5/1 are used as solvents. In some embodiments, the solvent for the washing is an alcohol, preferably methanol, ethanol or 2-propanol. In some embodiments, said alcohol is pure. In other embodiments, said alcohol contains a percentage of water, preferably in the range from about 5% to about 80, more preferably from about 10% to about 40% much more preferably from about 10% to about 30%. In some embodiments, the solvent is a solution of hydrochloric acid in water. According to such embodiments, the concentration of hydrochloric acid in water is preferably in the range from about 0.05M to about 2.0M, more preferably from about 0.1M to about 0.4M. In some embodiments, the purification is carried out using a mixture of the aforementioned solvents.

The purifications stages can be repeated several times and can use a single solvent or solvent mixture systems.

In one embodiment purification of 3,7-bis-(dimethylamino)-phenothiazin-5-ium chloride (MTC) or 3,7-dibromo-phenothiazin-5-ium bromide obtained from step (b), (c) or (d), can be carried out by crystallization.

Suitable solvents or solvent mixtures for crystallization include methanol, ethanol, 2-propanol, hydrochloric acid, water or mixtures thereof.

The crystallization can be repeated several times and can use a single solvents or solvent mixture systems.

In one embodiment, when the product obtained after steps (a), (b) and optionally (c) is 3,7-bis-(dimethylamino)-phenothiazin-5-ium bromide, in order to obtain 3,7-bis-(dimethylamino)-phenothiazin-5-ium chloride (MTC) said product must be eluted into an ion exchange column to exchange the bromide ion with the chloride ion. According to such embodiment, after the optional purification step (c), the product obtained from steps (a) to (b) is dissolved in a suitable solvent and is eluted through a column containing a macroporous anion exchange resin in an activated chloride form, to perform an anion exchange on the product (step (d)).

Suitable solvents to dissolve the product can be methanol, ethanol, 2-propanol, water or mixtures thereof. In some embodiments, a mixture of ethanol and water is used, the mixture having a v/v percentage of water ranging from about 1% to about 40%, more preferably from about 5% to about 35%, more preferably from about 8% to about 25%, much more preferably from about 9% to about 20%. In some embodiments, a mixture of methanol and water is used, the mixture having a v/v percentage of water ranging from about 1% to about 40%, more preferably from about 5% to about 35%, more preferably from about 8% to about 25%, much more preferably from about 9% to about 20%. In some embodiments, a mixture of 2-propanol and water is used, the mixture having a v/v percentage of water ranging from about 1% to about 40%, more preferably from about 5% to about 35%, more preferably from about 8% to about 25%, much more preferably from about 9% to about 20%. This solution is then eluted on a column filed with anion exchange resin in activated chloride form.

In one embodiment, the macroporous anion exchange resin is a macroporous polystyrene crosslinked with divinylbenzene containing quaternary ammonium groups.

In one embodiment the macroporous anion exchange resin is Purolite A500® in a chloride form.

In one embodiment, a final crystallization step of 3,7-bis-(dimethylamino)-phenothiazin-5-ium chloride can be carried out in an aqueous solution of hydrochloric acid, preferably in the concentration range from about 0.05M to about 2.0M, more preferably from about 0.1M to about 0.4M (steps (e) and (f)) In one embodiment, the purity of obtained products (3,7-bis-(dimethylamino)-phenothiazin-5-ium bromide and 3,7-bis-(dimethylamino)-phenothiazin-5-ium chloride (MTC) falls within the current, draft version and following updates for standards set out in the US and European pharmacopoeia monographs of 3,7-bis-(dimethylamino)-phenothiazin-5-ium chloride (MTC).

In one embodiment, the product of the present invention has very low metal content, for example, less than about 1 ppm arsenic, less than about 2 ppm copper and/or less than about 2 ppm zinc.

In one embodiment, the present invention therefore provides also for a 3,7-bis-(dimethylamino)-phenothiazin-5-ium chloride (MTC) or 3,7-bis-(dimethylamino)-phenothiazin-5-ium bromide having a purity higher than about 97% and less than about 1 ppm of arsenic.

In another embodiment, the present invention also provides for a 3,7-bis-(dimethylamino)-phenothiazin-5-ium chloride (MTC) or 3,7-bis-(dimethylamino)-phenothiazin-5-ium bromide having a purity higher than about 97% and less than about 2 ppm copper and less than about 2 ppm zinc.

In another embodiment, the present invention also provides for a 3,7-bis-(dimethylamino)-phenothiazin-5-ium chloride (MTC) or 3,7-bis-(dimethylamino)-phenothiazin-5-ium bromide having a purity higher than about 97%, less than 1 about ppm arsenic, less than about 2 ppm copper and less than about 2 ppm zinc.

In one further embodiment, the present invention also provides for a 3,7-bis-(dimethylamino)-phenothiazin-5-ium chloride (MTC) or 3,7-bis-(dimethylamino)-phenothiazin-5-ium bromide obtained or obtainable from the process for producing 3,7-bis-(dimethylamino)-phenothiazin-5-ium chloride or bromide as above disclosed.

In one further embodiment, the present invention provides the compound obtained from the step (a) of the Scheme 6, namely 3,7-dichlorophenotiazin-5-ium chloride as such.

In one further embodiment, the present invention provides the compound obtained from the step (a) of the Scheme 6, namely 3,7-dichlorophenotiazin-5-ium chloride as intermediate of a process for the production of 3,7-bis-(dimethylamino)-phenothiazin-5-ium chloride.

In one further embodiment, the present invention provides for a pharmaceutical composition containing a 3,7-bis-(dimethylamino)-phenothiazin-5-ium chloride (MTC) or the 3,7-bis-(dimethylamino)-phenothiazin-5-ium bromide having the characteristics as above disclosed in term of purity/metals and/or obtained or obtainable from the process for producing 3,7-bis-(dimethylamino)-phenothiazin-5-ium chloride or bromide as above disclosed.

In one further embodiment, the present invention provides for a 3,7-bis-(dimethylamino)-phenothiazin-5-ium chloride (MTC) or bromide as above disclosed or a pharmaceutical composition as above disclosed for use in diagnostic field, preferably in the gastro-intestinal endoscopy evaluation of inflammatory, ulcerative, pre-neoplastic, neoplastic, dysplastic pathologies and/or lesion of the gastro-intestinal tract. According to such an embodiment, the invention is able to ensure enhancing the detection of intestinal mucosal lesions as, for example, cancerous forms, pre-cancerous forms, interval cancers, adenomas, carcinomas, serrated lesions, intraepithelial neoplasia, dysplasia, polyps, pseudo-polyps, pre-polyps or different inflammatory pathologies, lesions sessile, flat or pedunculated shaped.

EXAMPLES

Example 1. Crude 3,7-bis-(dimethylamino)-phenothiazin-5-ium-bromide

Into a cooled reaction vessel (under 10° C.) phenothiazine (10.86 kg), ethyl acetate (216 liters) and catalyst, iron (III) chloride (30 g), were added. The reaction mixture was cooled (under 10° C.) and bromine (21.84 kg, 7.0 liters) in ethyl acetate (21.0 liters) was then added. The reaction temperature was kept within the range −10° C. to −15° C. After addition of all the bromine, the reaction mixture was stirred for an additional one hour at a temperature of −10° C. to −15° C.

Then, dimethylamine (19.0 kg) in ethyl acetate (77 liters) was added and the reaction temperature was kept within the range from −15° C. to +10° C. After addition of all of the dimethylamine, the reaction mixture was stirred for an additional two hours at a temperature of −15° C. to +10° C.

The raw product was filtered off, washed with cooled ethyl acetate and with 0.1 M hydrochloric acid. The isolated product was then purified using the below described methods.

Example 1 BIS. Crude 3,7-bis-(dimethylamino)-phenothiazin-5-ium-bromide

Into a cooled reaction vessel (under 10° C.) phenothiazine (10.86 kg), ethyl acetate (216 liters) and catalyst, iron (III) chloride (30 g), were added. The reaction mixture was cooled (under 10° C.) and bromine (21.84 kg, 7.0 liters) in ethyl acetate (21.0 liters) was then added. The reaction temperature was kept within the range −10° C. to −15° C. After addition of all the bromine, the reaction mixture was stirred for an additional one hour at a temperature of −10° C. to −15° C.

Then, dimethylamine (19.0 kg) in methanol (77 liters) was added and the reaction temperature was kept within the range from −15° C. to +10° C. After addition of all of the dimethylamine, the reaction mixture was stirred for an additional two hours at a temperature of −15° C. to +10° C.

The raw product was filtered off, washed with cooled ethyl acetate and with 0.1 M hydrochloric acid. The isolated product was then purified using the below described methods.

Example 2. Crude 3,7-bis-(dimethylamino)-phenothiazin-5-ium chloride

To a cooled reaction vessel (under 10° C.) phenothiazine (10.86 g), ethyl acetate (250 ml) and catalyst, iron (III) chloride (30 mg) were added. The reaction mixture was cooled (under 10° C.) and gaseous chlorine (9.66 g, condensed by −30° C.) was added. The reaction temperature was kept within the range −10° C. to −15° C. After addition of all of the chlorine the reaction mixture was stirred for an additional hour at temperature within the range −10° C. to −15° C.

Then, dimethylamine (19.0 g) in ethylacetate (77 ml) was added and the reaction temperature was kept within the range −15° C. to +10° C. After addition of all of the dimethylamine, the reaction mixture was stirred for additional two hours at a temperature within the range −15° C. to +10° C.

The raw product was filtered off, washed with cooled ethyl acetate and with 0.1 M hydrochloric acid. The isolated product was then purified using the below described methods with aliquot volumes of solvents.

Example 3. Purified 3,7-bis-(dimethylamino)-phenothiazin-5-ium chloride from Crude 3,7-bis(dimethylamino)-phenothiazin-5-ium bromide The isolated product from Example I (3,7-bis(dimethylamino)-phenothiazin-5-ium bromide) was washed under stirring in 2-propanol (60 liters) at room temperature for one hour, and filtered off. 2-propanol was added and washing under stirring was repeated at temperature of about 50° C., the mixture was cooled to room temperature and filtered off.

At the end a mixture of 2-propanol (12 liters) and 0.5 M hydrochloric acid (48 liters) was added and the slurry procedure was repeated at temperature of about 50° C. The mixture was cooled to room temperature and filtered off.

The product was dissolved in mixture of 2-propanol (100 liters) and water (20 liters) at 60° C. and eluted through an anion exchange resin column (45 liters of Purolite A500, chloride form); then the eluates were concentrated by evaporation. The dry product was dissolved in 0.4 M hydrochloric acid (100 liters) at 60° C. and then cooled at 10° C., the solution was stirred at this temperature for two hours and the product was filtered off and dried. Yield 9.6 kg.

The $^{13}C$ and $^1H$-NMR spectra ($(CD_3)_2SO$; 600 MHz) of this product confirm the structure of the compound. $^1H$-NMR spectrum (values in ppm): 3.34 (s, 12H, 2×N(CH$_3$)$_2$, 7.43 (m, 4H, aromatics; 2, 4, 6 and 8 CH), 7.83 (d, 2H, aromatics; 1 and 9 CH). $^{13}C$ NMR spectrum (values in ppm): 41.1 (N(CH$_3$)$_2$), 106.8 (4 and 6 CH), 119.0 (2 and 8 CH), 133.5 (12 and 13 C̲S*), 134.9 (11 and 14 C̲N), 137.8 (1 and 9 CH) and 153.8 (3 and 7 C̲—N(CH$_3$)$_2$).

Example 4. Purified 3,7-bis-(dimethylamino)-phenothiazin-5-ium chloride from Crude 3,7-bis(dimethylamino)-phenothiazin-5-ium bromide The isolated product from Example I (3,7-bis(dimethylamino)-phenothiazin-5-ium bromide) was slurried in ethanol (60 liters) at room temperature for one hour and filtered off. Ethanol was added and slurry procedure was repeated at temperature of about 50° C. The mixture was cooled to room temperature and filtered off.

At the end a mixture of ethanol (12 liters) was added and 0.5 M hydrochloric acid (48 liters) and the slurry procedure was repeated at temperature of about 50° C. The mixture was cooled to room temperature and filtered off.

The product was dissolved in a mixture of ethanol (100 liters) and water (20 liters) at 60° C. and eluted through a column packed with a anion exchange resin (45 liters of Purolite A500, chloride form); then the eluted fractions were evaporated under vacuum to dryness. The dry product was dissolved in 0.4 M hydrochloric acid (100 liters) at 60° C. and cooled under 10° C., the solution was stirred at this temperature for two hours and the product was filtered off and dried. Yield 10.8 kg.

The registered $^{13}C$ and $^1H$-NMR spectra ($(CD_3)_2SO$; 600 MHz) confirm the structure of the examined compound: the NMR signals are practically superimposeable to those obtained by the analysis of the sample isolated by the example 3.

Example 5. Purified 3,7-bis-(dimethylamino)-phenothiazin-5-ium chloride from Crude 3,7-bis(dimethylamino)-phenothiazin-5-ium bromide The isolated product from Example 1 (3,7-bis(dimethylamino)-phenothiazin-5-ium bromide) was slurried in methanol (60 liters) at room temperature for one hour and filtered off. Methanol was added and the slurry procedure was repeated at temperature of about 50° C. The mixture was cooled to room temperature and filtered off.

At the end a mixture of methanol (12 liters) and 0.5 M hydrochloric acid (48 liters) was added and the slurry procedure was repeated at temperature of about 50° C. The mixture was cooled to room temperature and filtered off.

The product was dissolved in mixture of methanol (100 liters) and water (20 liters) at 60° C. and eluted through a column filed with an anionic exchange resin (45 liters of Purolite A500, chloride form); then the collected eluates were concentrated by evaporation. The dry product was dissolved in 0.2 M hydrochloric acid (100 liters) at 60° C. and cooled under 10° C. The solution was stirred at this temperature two hours and the product was filtered off and dried. Yield 12.4 kg.

The $^{13}C$ and $^1H$-NMR spectra ($(CD_3)_2SO$; 600 MHz) registered on this product confirm the structure of the compound: the NMR signals are practically superimposeable to those obtained by the analysis of the samples isolated by the examples 3 and 4.

Example 6. Comparative Example: Preparation of Purified 3,7-bis-(dimethylamino)-phenothiazin-5-ium-bromide without the Use of FeCl$_3$ Into a cooled reaction vessel (under 10° C.) phenothiazine (10.86 kg) and ethyl acetate (216 liters) were added. The reaction mixture was cooled (under 10° C.) and bromine (21.84 kg, 7.0 liters) in ethyl acetate (21.0 liters) was then added. The reaction temperature was kept within the range −10° C. to −15° C. After addition of all the bromine, the reaction mixture was stirred for an additional two hours at a temperature of −10° C. to −15° C.

Then, dimethylamine (19.0 kg) in ethyl acetate (77 liters) was added and the reaction temperature was kept within the range from −15° C. to +10° C. After addition of all of the dimethylamine, the reaction mixture was stirred for an additional two hours at a temperature of −15° C. to +10° C.

The raw product was filtered off, washed with cooled ethyl acetate and with 0.1 M hydrochloric acid.

The isolated raw product (3,7-bis(dimethylamino)-phenothiazin-5-ium bromide) was slurried in methanol (60 liters) at room temperature for one hour and filtered off. Methanol was added and the slurry procedure was repeated at temperature of about 50° C. The mixture was cooled to room temperature and filtered off.

At the end a mixture of methanol (12 liters) and 0.5 M hydrochloric acid (48 liters) was added and the slurry was repeated at temperature of about 50° C. The mixture was cooled to room temperature and filtered off.

The product was dissolved in mixture of methanol (100 liters) and water (20 liters) at 60° C. and eluted through a column filed with an anionic exchange resin (45 liters of Purolite A500, chloride form); then the collected eluates were concentrated by evaporation. The dry product was dissolved in 0.2 M hydrochloric acid (100 liters) at 60° C. and cooled under 10° C. The solution was stirred at this temperature two hours and the product was filtered off and dried. Yield 11.1 kg.

The $^{13}C$ and $^{1}H$-NMR spectra (($CD_3$)$_2SO$; 600 MHz) registered on this product confirm the structure of the compound: the NMR signals are practically superimposeable to those obtained by the analysis of the samples isolated by the examples 3, 4 and 5.

TABLE 1

Relevant Analytical Results of samples obtained according to the above Examples 3-5

|  | Example 3 | Example 4 | Example 5 |
|---|---|---|---|
| Product % HPLC | 97.35 | 97.65 | 97.58 |
| Impurity A % HPLC * | 2.26 | 2.10 | 2.06 |
| Total other impurities % HPLC | 0.39 | 0.25 | 0.36 |
| Arsenic ppm | <1 | <1 | <1 |
| Copper ppm | <2 | <2 | <2 |
| Zinc ppm | <2 | <2 | <2 |
| Iron ppm | 35.8 | 31.5 | 28.9 |
| Bromides | absent | absent | absent |

* HPLC methods and specifications according to PhEur

What is claimed is:

1. A process for producing 3,7-bis-(dimethylamino)-phenothiazin-5-ium chloride or bromide comprising the steps of:
   a) reacting chlorine or bromine with phenothiazine, to produce 3,7-dichloro-phenothiazin-5-ium chloride or 3,7-dibromo-phenothiazin-5-ium bromide respectively;
   b) adding dimethylamine to the reaction mixture of step a), to produce 3,7-bis-(dimethylamino)-phenothiazin-5-ium chloride or 3,7-bis-(dimethylamino)-phenothiazin-5-ium bromide respectively;
   wherein steps a) and b) are carried out without isolation and/or purification of the intermediate formed in step a);
   wherein step a) is carried out at a temperature of less than about 10° C.;
   wherein step b) is carried out in a suitable solvent system selected from dichloromethane, acetic acid, methylacetate, ethylacetate, butylacetate, chloroform or mixtures thereof; and
   wherein step a) is carried out in the presence of a metal catalyst.

2. The process of claim 1, wherein step a) is carried out at a temperature of less than about 5° C.; or less than about 0° C., or less than about −10° C., between about −20° C. and about −10° C., or at about −15° C.; and further optionally wherein step b) is carried out at a temperature of less than about 20° C., or less than about 10° C., or between about −20° C. and about 10° C., or at about −15° C.

3. The process of claim 1 or 2, wherein step a) is carried out in ethylacetate; and optionally wherein step b) is carried out in a solvent system selected from methanol, water, ethylacetate, butylacetate or mixtures thereof, or selected from methanol, ethylacetate or mixtures thereof.

4. The process of claim 2, wherein step a) is carried out at a temperature of between about −20° C. and about −10° C. and step b) is carried out at a temperature of between about −20° C. and about 10° C.

5. The process of claim 1, the metal catalyst is an iron salt; or iron (III) chloride, or iron (II) sulfate.

6. The process of claim 1, further comprising step c):
   c) purifying the 3,7-bis-(dimethylamino)-phenothiazin-5-ium chloride or 3,7-bis-(dimethylamino)-phenothiazin-5-ium bromide obtained in step b); optionally wherein the purification step c) further comprises slurring the 3,7-bis-(dimethylamino)-phenothiazin-5-ium chloride or 3,7-bis-(dimethylamino)-phenothiazin-5-ium bromide obtained in step b) with dichloromethane, methylacetate, ethylacetate, butyl acetate, methanol, ethanol, 2-propanol, aqueous hydrochloric acid, water or mixtures thereof.

7. The process of claim 1 further comprising:
   eluting the 3,7-bis-(dimethylamino)-phenothiazin-5-ium bromide obtained in step b) through an ion exchange column, to exchange bromide with chloride.

8. The process of claim 1 further comprising:
   dissolving the 3,7-bis-(dimethylamino)-phenothiazin-5-ium chloride or 3,7-bis-(dimethylamino)-phenothiazin-5-ium bromide obtained in step b) in an aqueous solution of hydrochloric acid and filtering the solution of 3,7-bis-(dimethylamino)-phenothiazin-5-ium chloride or 3,7-bis-(dimethylamino)-phenothiazin-5-ium bromide.

9. The process of claim 1 further comprising:
   crystallizing the 3,7-bis-(dimethylamino)-phenothiazin-5-ium chloride or 3,7-bis-(dimethylamino)-phenothiazin-5-ium bromide obtained in step b), wherein the crystallization is carried out in methanol, ethanol, 2-propanol, aqueous hydrochloric acid, water or mixtures thereof.

10. The process of claim 3, wherein the solvent system in step b) is methanol or ethylacetate or mixtures thereof.

11. The process of claim 6, wherein purification step c) is conducted at a temperature of from about −5° C. to about 60°.

12. The process of claim 8, wherein hydrochloric acid is at a concentration from about 0.05 molar to about 2.0 molar solution.

13. The process of claim 9, wherein the crystallization is carried out in hydrochloric acid at a concentration from about 0.05 molar to about 2.0 molar solution in water.

14. The process of claim 6 further comprising step d):
   d) eluting the purified 3,7-bis-(dimethylamino)-phenothiazin-5-ium bromide obtained in step c) through an ion exchange column, to exchange bromide with chloride.

15. The process of claim 6 further comprising:
   crystallizing the purified 3,7-bis-(dimethylamino)-phenothiazin-5-ium chloride or 3,7-bis-(dimethylamino)-phenothiazin-5-ium bromide obtained in step c), wherein the crystallization is carried out in methanol, ethanol, 2-propanol, aqueous hydrochloric acid, water or mixtures thereof.

16. The process of claim 15, wherein the crystallization is carried out in hydrochloric acid at a concentration from about 0.05 molar to about 2.0 molar solution in water.

17. The process of claim 7 further comprising:
   crystallizing the 3,7-bis-(dimethylamino)-phenothiazin-5-ium chloride, wherein the crystallization is carried out in methanol, ethanol, 2-propanol, aqueous hydrochloric acid, water or mixtures thereof.

18. The process of claim 17, wherein the crystallization is carried out in hydrochloric acid at a concentration from about 0.05 molar to about 2.0 molar solution in water.

* * * * *